United States Patent
Stigall et al.

(10) Patent No.: US 11,589,835 B2
(45) Date of Patent: Feb. 28, 2023

(54) FREQUENCY-TUNABLE INTRALUMINAL ULTRASOUND DEVICE

(71) Applicant: KONINKLIJKE PHILIPS N.V., Eindhoven (NL)

(72) Inventors: Jeremy Stigall, Carlsbad, CA (US); Princeton Saroha, Ladera Ranch, CA (US); Robert Emmett Kearney, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 549 days.

(21) Appl. No.: 15/998,442

(22) Filed: Aug. 15, 2018

(65) Prior Publication Data

US 2019/0053781 A1 Feb. 21, 2019

Related U.S. Application Data

(60) Provisional application No. 62/545,954, filed on Aug. 15, 2017.

(51) Int. Cl.
*A61B 8/12* (2006.01)
*A61B 8/08* (2006.01)
(Continued)

(52) U.S. Cl.
CPC ............... *A61B 8/12* (2013.01); *A61B 1/015* (2013.01); *A61B 8/4483* (2013.01);
(Continued)

(58) Field of Classification Search
None
See application file for complete search history.

(56) References Cited

U.S. PATENT DOCUMENTS 5,558,092 A  9/1996 Unger
6,049,958 A * 4/2000 Eberle .................. A61B 1/0011
                                                    29/25.35

(Continued)

FOREIGN PATENT DOCUMENTS

| EP | 2455133 A1 | 5/2012 |
| JP | 2004290548 A | 10/2004 |
| WO | 2017001965 A1 | 1/2017 |

OTHER PUBLICATIONS

Shung, "Diagnostic Ultrasound: Imaging and Blood Flow Measurements" 2006 (Year: 2006).*

*Primary Examiner* — Colin T. Sakamoto

(57) ABSTRACT

Intraluminal ultrasound devices, systems and methods are provided. In one embodiment, an intraluminal ultrasound device includes a flexible elongate member configured to be positioned within a body lumen of a patient, the flexible elongate member including a distal portion and a longitudinal axis; and a transducer array disposed at the distal portion of the flexible elongate member and circumferentially positioned around the longitudinal axis of the flexible elongate member. The transducer array includes a plurality of micromachined ultrasound transducers (MUTs). In addition, the transducer array is configured to obtain ultrasound imaging data of the body lumen in response to a first electrical signal, and apply an ultrasound therapy within the body lumen in response to a second electrical signal.

21 Claims, 7 Drawing Sheets

(51) Int. Cl.

| | | |
|---|---|---|
| *A61N 7/00* | (2006.01) | |
| *A61B 8/00* | (2006.01) | |
| *A61M 37/00* | (2006.01) | |
| *A61N 7/02* | (2006.01) | |
| *A61B 1/015* | (2006.01) | |
| *A61B 18/14* | (2006.01) | |
| *A61B 18/00* | (2006.01) | |
| *A61B 17/22* | (2006.01) | |
| *A61B 90/00* | (2016.01) | |
| *A61B 34/00* | (2016.01) | |
| *A61B 17/3207* | (2006.01) | |
| *A61M 25/00* | (2006.01) | |

(52) U.S. Cl.
CPC .......... *A61B 8/4488* (2013.01); *A61B 8/5223* (2013.01); *A61B 8/54* (2013.01); *A61B 8/56* (2013.01); *A61M 37/0092* (2013.01); *A61N 7/00* (2013.01); *A61N 7/02* (2013.01); *A61N 7/022* (2013.01); *A61B 17/22* (2013.01); *A61B 17/2202* (2013.01); *A61B 17/320758* (2013.01); *A61B 18/14* (2013.01); *A61B 34/25* (2016.02); *A61B 2018/00577* (2013.01); *A61B 2018/00601* (2013.01); *A61B 2090/378* (2016.02); *A61B 2218/007* (2013.01); *A61M 25/00* (2013.01); *A61N 2007/0043* (2013.01); *A61N 2007/0052* (2013.01); *A61N 2007/0073* (2013.01)

(56) References Cited

U.S. PATENT DOCUMENTS

| | | | |
|---|---|---|---|
| 6,200,268 B1 | 3/2001 | Vince et al. | |
| 6,381,350 B1 | 4/2002 | Klingensmith et al. | |
| 6,740,039 B1* | 5/2004 | Rafter | A61B 8/463 600/439 |
| 7,074,188 B2 | 7/2006 | Nair et al. | |
| 7,175,597 B2 | 2/2007 | Vince et al. | |
| 7,215,802 B2 | 5/2007 | Klingensmith et al. | |
| 7,359,554 B2 | 4/2008 | Klingensmith et al. | |
| 7,463,759 B2 | 12/2008 | Klingensmith et al. | |
| 2002/0127181 A1* | 9/2002 | Edwards | A61K 51/0497 534/10 |
| 2006/0036167 A1* | 2/2006 | Shina | A61B 6/481 600/433 |
| 2006/0184069 A1 | 8/2006 | Vaitekunas | |
| 2007/0035204 A1* | 2/2007 | Angelsen | B06B 1/064 310/311 |
| 2007/0073135 A1* | 3/2007 | Lee | A61B 8/4488 600/407 |
| 2007/0287918 A1* | 12/2007 | Huang | B06B 1/0292 367/181 |
| 2008/0221448 A1 | 9/2008 | Khuri-Yakub | |
| 2010/0168569 A1* | 7/2010 | Sliwa | A61B 8/0841 606/41 |
| 2011/0213248 A1 | 9/2011 | Murakami et al. | |
| 2011/0257523 A1* | 10/2011 | Hastings | A61B 8/12 600/439 |
| 2012/0265227 A1* | 10/2012 | Sverdlik | A61M 25/10 606/169 |
| 2013/0163383 A1 | 6/2013 | Murakami | |
| 2014/0005521 A1* | 1/2014 | Kohler | A61B 5/4836 600/411 |
| 2014/0058294 A1 | 2/2014 | Gross et al. | |
| 2015/0065922 A1 | 3/2015 | Kohler | |
| 2015/0366508 A1* | 12/2015 | Chou | A61B 8/4477 600/374 |
| 2016/0008636 A1* | 1/2016 | Warnking | A61B 8/445 600/411 |
| 2016/0029999 A1 | 2/2016 | Corl | |
| 2016/0199030 A1* | 7/2016 | Patil | H02N 1/006 600/459 |
| 2017/0119348 A1 | 5/2017 | Degertekin | |
| 2017/0360397 A1* | 12/2017 | Rothberg | A61B 8/4483 |

\* cited by examiner

FREQUENCY-TUNABLE INTRALUMINAL ULTRASOUND DEVICE

TECHNICAL FIELD

The present disclosure relates generally to intraluminal ultrasound device and, in particular, intraluminal ultrasound device with ultrasound transducer array tunable for both imaging and therapeutic application.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy with frequencies higher than 10 MHz to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Ultrasound has been used in some drug delivery and therapeutic applications. Conventionally, due to the different in operation frequencies between the two, an ultrasound imaging device and an ultrasound therapeutic device are separate and distinct. In the case of intravascular imaging and therapy, both the ultrasound imaging device and the ultrasound therapeutic device have to be inserted into and withdrawn from the patient's blood vessel at least once during a procedure workflow. To evaluate the effectiveness of an ultrasound therapy, the intravascular therapy device has to be withdrawn from the patient's blood vessel, and the imaging device has to be re-inserted in to the blood vessel. This multiplicity of insertion and withdrawal of ultrasound devices not only is time-consuming but also can increase chances of clinical complications, such as blood vessel damage.

SUMMARY

Embodiments of the present disclosure provide an intraluminal ultrasound device that includes a transducer array with a plurality of subarrays interconnected by flexible circuits. The transducer array is configured to obtain ultrasound imaging data in response to a first electrical signal and to apply an ultrasound therapy in response to a second electrical signal. Each of the subarrays includes a plurality of micromachined ultrasound transducers (MUTs). The transducer array operates at a first frequency range in response to the first electrical signal and at a second frequency range in response to the second electrical signal. The first frequency range is different from the second frequency.

In one embodiment, an intraluminal ultrasound device includes a flexible elongate member configured to be positioned within a body lumen of a patient, the flexible elongate member including a distal portion and a longitudinal axis; and a transducer array disposed at the distal portion of the flexible elongate member and circumferentially positioned around the longitudinal axis of the flexible elongate member. The transducer array includes a plurality of micromachined ultrasound transducers (MUTs). In addition, the transducer array is configured to obtain ultrasound imaging data of the body lumen in response to a first electrical signal, and apply an ultrasound therapy within the body lumen in response to a second electrical signal. Additional aspects, features, and advantages of the present disclosure will become apparent from the following detailed description.

In some embodiments, the transducer array of the intraluminal ultrasound device, in response to the first electrical signal, operates at a first frequency range and in response to the second electrical signal, operates at a second frequency range different from the first electrical frequency range. In some embodiments, the first frequency range and the second frequency range do not overlap. In some embodiments, the first frequency range includes frequencies between 10 MHz and 70 MHz and the second frequency range includes frequencies between 1 KHz and 20 MHz. In some embodiments, the plurality of MUTs includes a plurality of subarrays of MUTs interconnected by a plurality of flexible circuits. In some implementations, the intraluminal ultrasound device further includes a control circuit in communication with the transducer array and the control circuit is configured to generate the first electrical signal and the second electrical signal. In some instances, a voltage of the first electrical signal is different than a voltage of the second electrical signal. In some instances, the plurality of MUTs comprises a plurality of piezoelectric micromachined ultrasound transducers (PMUTs). In some other instances, the plurality of MUTs comprises a plurality of capacitive micromachined ultrasound transducers (CMUTs). In some implementations, the plurality of CMUTs operates under a bias voltage. In some instances, the bias voltage is controlled by the control circuit. In one embodiment, the plurality of MUTs of the intraluminal ultrasound device includes a first plurality of PMUTs and a second plurality of PMUTs. Each of the first plurality of PMUTs includes a transducer membrane of a first thickness, and each of the second plurality of PMUTs includes a transducer membrane of a second thickness different from the first thickness. In another embodiment, the plurality of MUTs of the intraluminal ultrasound device includes a first plurality of CMUTs and a second plurality of CMUTs. Each of the first plurality of CMUTs operates under a first bias voltage, and each of the second plurality of CMUTs operates under a second bias voltage different from the first bias voltage. In some instances, one of the first and second bias voltages is zero volts. In some implementations, the plurality of MUTs of the intraluminal ultrasound device includes a plurality of CMUTs and a plurality of PMUTs.

In another embodiment, a method for treating a target site within a body lumen of a patient is provided. The method includes: obtaining ultrasound imaging data of the body lumen with a transducer array operating at a first frequency range, the transducer array disposed at a distal portion of a flexible elongate member of an intraluminal ultrasound device; and applying the ultrasound therapy to the target site within the body lumen with the transducer array operating at a second frequency range. The intraluminal ultrasound device includes the flexible elongate member configured to be positioned within the body lumen of the patient, the flexible elongate member including the distal portion and a longitudinal axis; and the transducer array disposed at the distal portion of the flexible elongate member and circumferentially positioned around the longitudinal axis of the flexible elongate member. In some embodiments, the transducer array is configured to obtain ultrasound imaging data of the body lumen in response to a first electrical signal, and apply an ultrasound therapy within the body lumen in response to a second electrical signal. The transducer array includes a plurality of MUTs.

In some instances, the intraluminal ultrasound device is in communication with an ultrasound processing system and the method further comprises: after obtaining ultrasound imaging data of the body lumen, determining by the ultrasound processing system, a diameter of the body lumen and a level of calcification of the target site based on the obtained ultrasound imaging data; and modifying the second electrical signal based on the determined diameter of the body lumen and the level of calcification of the target site. In some embodiments, the method further includes after applying the ultrasound therapy to the target site, obtaining ultrasound imaging data of the body lumen using the transducer array; determining, by using the ultrasound processing system, an updated diameter of the body lumen and an updated level of calcification of the target site based on the obtained ultrasound imaging data; modifying the second electrical signal based on the updated diameter of the body lumen and the updated level of calcification of the target site; and applying the ultrasound therapy to the target site within the body lumen with the transducer array. In some implementations, the method further includes treating the target site with a treatment catheter, wherein the treat catheter comprises a balloon catheter, a stent placement catheter, a drug delivery catheter, an ablation catheter, or a catheter with electrodes.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
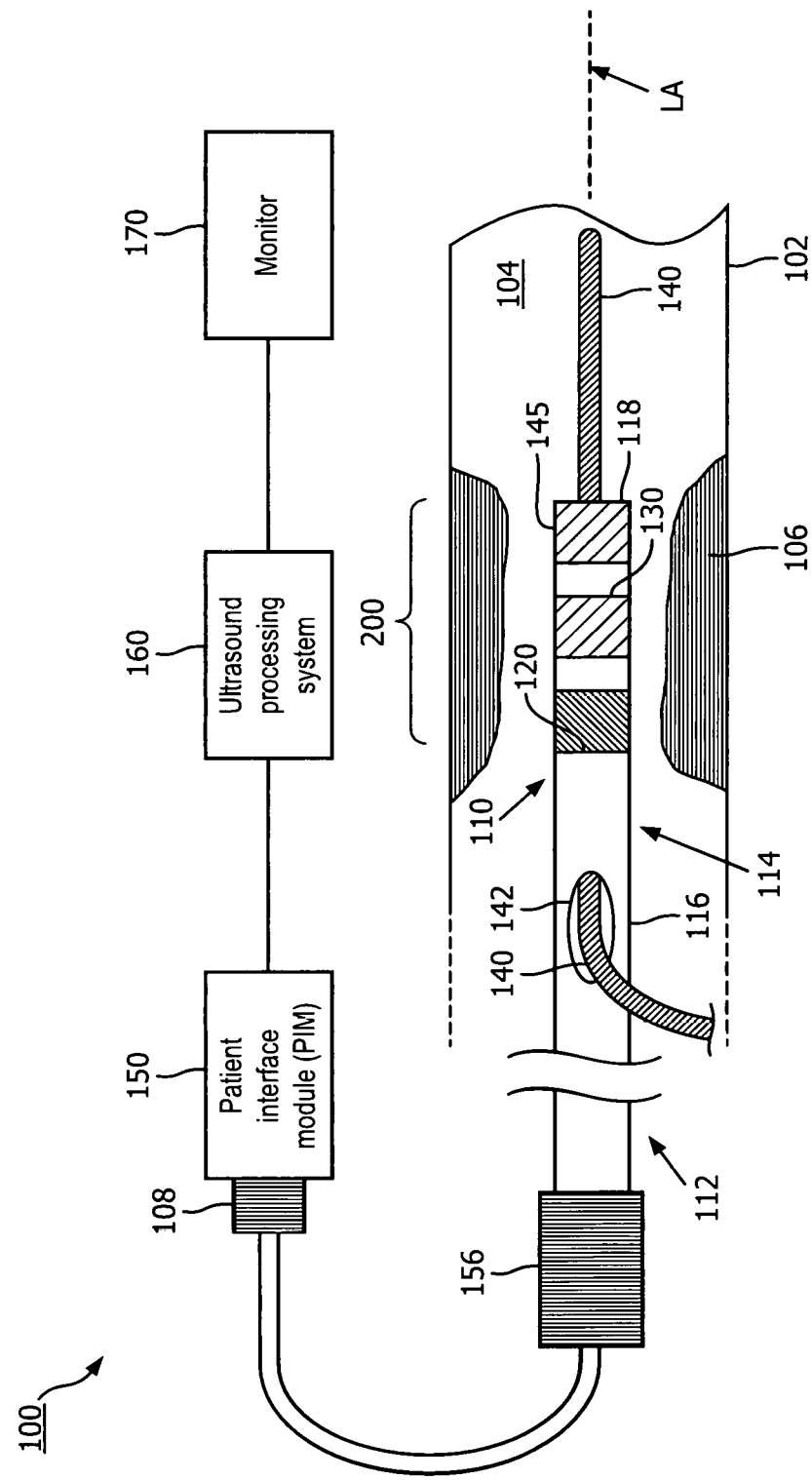
FIG. 1 is a diagrammatic schematic view of an ultrasound system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the ICE system is described in terms of intraluminal imaging, it is understood that it is not intended to be limited to this application. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound system 100 according to some embodiments of the present disclosure. The system 100 can include an ultrasound device 110, a patient interface module (PIM) 150, an ultrasound processing system 160 (sometimes referred to as a computer system), and/or a monitor 170. The ultrasound device 110 is structurally arranged (e.g., sized and/or shaped) to be positioned within anatomy 102 of a patient. The ultrasound device 110 obtains ultrasound imaging data from within the anatomy 102 and applies ultrasound therapy to the anatomy 102. The ultrasound processing system 160 comprises at least a processor and is configured to control the acquisition of ultrasound imaging data and/or the application of ultrasound therapy, and to generate images of the anatomy 102 (using the ultrasound imaging data received via the PIM 150) that is displayed on the monitor 170. The processing system 160 is configured to control the ultrasound imaging and application of ultrasound therapy alternatively or simultaneously. Optionally, the processing system can be configured to administer a pharmacological agent. In an embodiment, the ultrasound imaging and application of ultrasound therapy are performed simultaneously and the pharmacological agent is administered according to a dose that is determined based on real time ultrasound imaging data.

Generally, the ultrasound device 110 can be a catheter, a guide catheter, or a guide wire. The ultrasound device 110 includes a flexible elongate member 116. As used herein, "elongate member" or "flexible elongate member" includes at least any thin, long, flexible structure structurally arranged (e.g., sized and/or shaped) to be positioned within a lumen 104 (or body lumen) of the anatomy 102. For example, a distal portion 114 of the flexible elongate member 116 is positioned within the lumen 104, while a proximal portion 112 of the flexible elongate member 116 is positioned outside of the body of the patient. The flexible elongate member 116 can include a longitudinal axis LA. In some instances, the longitudinal axis LA can be a central longitudinal axis of the flexible elongate member 116. In some embodiments, the flexible elongate member 116 can include one or more polymer/plastic layers formed of various grades of nylon, Pebax, polymer composites, polyimides, and/or Teflon. In some embodiments, the flexible elongate member 116 can include one or more layers of braided metallic and/or polymer strands. The braided layer(s) can be tightly or loosely braided in any suitable configuration, including any suitable per in count (pic). In some embodiments, the flexible elongate member 116 can include one or more metallic and/or polymer coils. All or a portion of the flexible elongate member 116 may have any suitable geometric cross-sectional profile (e.g., circular, oval, rectangular, square, elliptical, etc.) or non-geometric cross-sectional profile. For example, the flexible elongate member 116 can have a generally cylindrical profile with a circular cross-sectional profile that defines an outer diameter of the flexible elongate member 116. For example, the outer diameter of the flexible elongate member 116 can be any suitable value for positioning within the anatomy 102, including between approximately 1 Fr (0.33 mm) and approximately 15 Fr (5 mm), including values such as 3.5 Fr, 5 Fr, 7 Fr, 8.2 Fr, 9 Fr, and/or other suitable values both larger and smaller.

The ultrasound device 110 may or may not include one or more lumens extending along all or a portion of the length of the flexible elongate member 116. The lumen of the ultrasound device 110 can be structurally arranged (e.g., sized and/or shaped) to receive and/or guide one or more other diagnostic and/or therapeutic instruments. If the ultrasound device 110 includes lumen(s), the lumen(s) may be centered or offset with respect to the cross-sectional profile of the device 110. In the illustrated embodiment, the ultrasound device 110 is a catheter and includes a lumen at the distal portion 114 of the flexible elongate member 116. A guide wire 140 extends through the lumen of the ultrasound device 110 between an exit/entry port 142 and an exit/entry port at a distal end 118 of the flexible elongate member 116. Generally, the guide wire 140 is a thin, long, flexible structure that is structurally arranged (e.g., sized and/or shaped) to be disposed within the lumen 104 of the anatomy 102. During a diagnostic and/or therapeutic procedure, a medical professional typically first inserts the guide wire 140 into the lumen 104 of the anatomy 102 and moves the guide wire 140 to a desired location within the anatomy 102, such as adjacent to an occlusion 106. The guide wire 140 facilitates introduction and positioning of one or more other diagnostic and/or therapeutic instruments, including the ultrasound device 110, at the desired location within the anatomy 102. For example, the ultrasound device 110 moves through the lumen 104 of the anatomy 102 along the guide wire 140. In some embodiments, the lumen of the ultrasound device 110 can extend along the entire length of the flexible elongate member 116. In the illustrated embodiment, the exit/entry port 142 is positioned proximally of ultrasound components 120, 130, and 145 of the ultrasound device 110. In some embodiments, the exit/entry port 142, the exit/entry port at the distal end 118, and/or the lumen of the ultrasound device 110 is positioned distally of the ultrasound components 120, 130, and 145. In some embodiments, the ultrasound device 110 is not used with a guide wire, and the exit/entry port 142 can be omitted from the ultrasound device 110. For ease of reference, the assembly that includes the ultrasound components 120, 130, and 145 is referred to as the transducer assembly 200. The ultrasound components 120, 130 and 145 can sometimes be structures other than ultrasound transducers or an ultrasound transducer arrays and therefore can also be referred to as ultrasound structures 120, 130 and 145.

The anatomy 102 may represent any fluid-filled or surrounded structures, both natural and man-made. For example, the anatomy 102 can be within the body of a patient. Fluid can flow through the lumen 104 of the anatomy 102. In some instances, the ultrasound device 110 can be referenced as an intraluminal device. The anatomy 102 can be a vessel, such as a blood vessel, in which blood flows through the lumen 104. In some instances, the ultrasound device 110 can be referenced as an intravascular device. In various embodiments, the blood vessel is an artery or a vein of a patient's vascular system, including cardiac vasculature, peripheral vasculature, neural vasculature, renal vasculature, and/or any other suitable anatomy/lumen inside the body. The anatomy 102 can be tortuous in some instances. For example, the device 110 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 110 may be used to examine man-made structures such as, but without limitation, heart valves, stents, shunts, filters and other devices.

The occlusion 106 of the anatomy 102 is generally representative of any blockage or other structural arrangement that results in a restriction to the flow of fluid through the lumen 104, for example, in a manner that is deleterious to the health of the patient. For example, the occlusion 106 narrows the lumen 104 such that the cross-sectional area of the lumen 104 and/or the available space for fluid to flow through the lumen 104 is decreased. Where the anatomy 102 is a blood vessel, the occlusion 106 may be a result of plaque buildup, including without limitation plaque components such as fibrous, fibro-lipidic (fibro fatty), necrotic core, calcified (dense calcium), blood, fresh thrombus, and/or mature thrombus. In some instances, the occlusion 106 can be referenced as thrombus, a stenosis, and/or a lesion. Generally, the composition of the occlusion 106 will depend on the type of anatomy being evaluated. Healthier portions of the anatomy 102 may have a uniform or symmetrical profile (e.g., a cylindrical profile with a circular cross-sectional profile). The occlusion 106 may not have a uniform or symmetrical profile. Accordingly, diseased portions of the anatomy 102, with the occlusion 106, will have a non-symmetric and/or otherwise irregular profile. While the anatomy 102 is illustrated in FIG. 1 as having a single occlusion 106, it is understood that the devices, systems, and methods described herein have similar application for anatomy having multiple occlusions.

The ultrasound device 110 includes ultrasound components 120 and 130 at the distal portion 114 of the flexible elongate member 116. The ultrasound components 120 and 130 are configured to emit ultrasonic energy into the anatomy 102 while the ultrasound device 110 is positioned within the lumen 104. In some embodiments, the two ultrasound components 120 and 130 are distinct. In other embodiments, the two ultrasound components 120 and 130 are the same ultrasound component or part of the same ultrasound component. One of the ultrasound components 120, 130 is configured for diagnostic use, while the other of the ultrasound components 120, 130 is configured for therapeutic use. For example, the ultrasound components 120, 130 can emit different frequencies of ultrasonic energy into the anatomy 102 depending on whether the ultrasonic energy is being used for diagnosis, such as imaging, and/or treatment.

In some embodiments, the ultrasound components 120 and/or 130 include ultrasound transducer(s). For example, the ultrasound components 120 and/or 130 can be configured to generate and emit ultrasound energy into the anatomy 102 in response to being activated by an electrical signal. In some embodiments, the ultrasound components 120 and/or 130 include a single ultrasound transducer. In some embodiments, the ultrasound components 120 and/or 130 include an ultrasound transducer array including more than one ultrasound transducer. For example, an ultrasound transducer array can include any suitable number of individual transducers between 2 transducers and 1000 transducers, including values such as 2 transducers, 4 transducers, 36 transducers, 64 transducers, 128 transducers, 500 transducers, 812 transducers, and/or other values both larger and smaller. The ultrasound components 120 and/or 130 can be any suitable configuration, such as phased array including a planar array, a curved array, a circumferential array, an annular array, etc. For example, the ultrasound component 120 and/or 130 can be a one-dimensional array or a two-dimensional array in some instances. In some instances, the ultrasound components 120 and/or 130 can be a rotational ultrasound device. The active area of the ultrasound components 120 and/or 130 can include one or more transducer materials and/or one or more segments of ultrasound elements (e.g., one or more rows, one or more columns, and/or one or more orientations) that can be uniformly or independently controlled and activated. The active area of the ultrasound components 120 and/or 130 can be patterned or structured in various basic or complex geometries. The ultrasound components 120 and/or 130 can be disposed in a side-looking orientation (e.g., ultrasonic energy emitted perpendicular and/or orthogonal to the longitudinal axis LA) and/or a forward-looking looking orientation (e.g., ultrasonic energy emitted parallel to and/or along the longitudinal axis LA). In some instances, the ultrasound components 120 and/or 130 is structurally arranged to emit and/or receive ultrasonic energy at an oblique angle relative to the longitudinal axis LA, in a proximal or distal direction. In some embodiments, ultrasonic energy emission can be electronically steered by selective triggering of one or more transducer elements of the ultrasound component 120 and/or 130.

The ultrasound transducer(s) of the ultrasound components 120 and/or 130 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. Depending on the transducer material, the manufacturing process for ultrasound transducer(s) can include dicing, kerfing, grinding, sputtering, wafer technologies (e.g., SMA, sacrificial layer deposition), other suitable processes, and/or combinations thereof.

In some embodiments, the ultrasound component 120 is configured to obtain ultrasound imaging data associated with the anatomy 102, such as the occlusion 106. The ultrasound imaging data obtained by the ultrasound component 120 can be used by a medical professional to diagnose the patient, including evaluating the occlusion 106 of the anatomy 102. For imaging, the ultrasound component 120 can be configured to both emit ultrasonic energy into the lumen 104 and/or the anatomy 102, and to receive reflected ultrasound echoes representative of fluid and/or tissue of lumen 104 and/or the anatomy 102. As described herein, the ultrasound component 120 can be an ultrasound imaging element, such as an ultrasound transducer and/or an ultrasound transducer array. For example, the ultrasound component 120 generates and emits ultrasound energy into the anatomy 102 in response to transmission of an electrical signal to the ultrasound component 120. For imaging, the ultrasound component 120 generates and transmits an electrical signal representative of the received reflected ultrasound echoes from the anatomy 102 (e.g., to the PIM 150). In various embodiments, the ultrasound component 120 can obtain imaging data associated with intravascular ultrasound (IVUS) imaging, forward looking intravascular ultrasound (FL-IVUS) imaging, intravascular photoacoustic (IVPA) imaging, intracardiac echocardiography (ICE), transesophageal echocardiography (TEE), and/or other suitable imaging modalities.

For diagnosis and/or imaging, the center frequency of the ultrasound component 120 can be between 10 MHz and 70 MHz, for example, including values such as 10 MHz, 20 MHz, 40 MHz, 45 MHz, 60 MHz, and/or other suitable values both larger and smaller. For example, lower frequencies (e.g., 10 MHz, 20 MHz) can advantageously penetrate further into the anatomy 102, such that more of the anatomy 102 is visible in the ultrasound images. Higher frequencies (e.g., 45 MHz, 60 MHz) can be better suited to generate more detailed ultrasound images of the anatomy 102 and/or fluid within the lumen 104. In some embodiments, the frequency of the ultrasound component 120 is tunable. For imaging, in some instances, the ultrasound component 120 can be tuned to receive wavelengths associated with the center frequency and/or one or more harmonics of the center frequency. In some instances, the frequency of the emitted ultrasonic energy can be modified by the voltage of the applied electrical signal and/or the application of a biasing voltage to the ultrasound component 120.

In some embodiments, the ultrasound component 130 is configured to apply an ultrasound therapy to the anatomy 102, such as the occlusion 106. For example, the ultrasound component 130 emits sound waves that damage the structure of the occlusion 106. In that regard, the ultrasound device 110 and/or the ultrasound component 130 can be referenced as a lithotripsy device. The ultrasonic energy emitted by the ultrasound component 130 can create micro fractures in the calcium blockage of occlusion 106. For example, the ultrasound component 130 can deliver ultrasonic energy in a targeted manner to cause cavitation (e.g., wave force cavitation, thermal cavitation, etc.) of the occlusion 106. Delivery of ultrasound therapy by the ultrasound component 130 advantageously facilitates thrombus dilution and/or vessel preparation. For example, ultrasound therapy can be applied prior to delivery of a pharmacological agent to the anatomy 102 or simultaneously with the ultrasound therapy. The pharmacological agent can be a thrombolytic agent, a fibrinolytic agent, plasmin, plasmid, tissue plasminogen activator, urokinase, streptokinase, collagenace, hepranoid, antithrombin drug, any other suitable drug, and/or combinations thereof. As described herein, Pharmacological uptake can be advantageously improved as a result of the degradation of the occlusion 106 by the ultrasonic energy. By compromising the structure of the occlusion 106, additional surface area is available for the pharmacological agent to contact and/or penetrate the anatomy 102. In an embodiment the ultrasound imaging, ultrasound treatment and administering the pharmacological agent occurs simultaneously. Based on the real time ultrasound imaging data the ultrasound treatment parameters may be adapted, as well as dosing the pharmacological agent. In an example, the occlusion 106 is imaged with the ultrasound as ultrasound treatment is commenced. At the initial phase a steady dose of pharmacological agent is released. Upon ultrasound treatment micro fractures appear in the occlusion, which change the echogenicity of the occlusion in the ultrasound image, based on which the dose of the pharmacological agent is updated, as a higher dose of the agent can more effectively interact with the occlusion through the micro fractures. As the occlusion material is dissolved through the combined treatment, the occlusion shrinks, which is detectable on the ultrasound imaging data. The dose of the pharmacological agent can be at that moment reduced and administered at a rate that is necessary, based on the size and the echogenic characteristic of the occlusion in real time. Accordingly, the efficacy of the treatment and the health of the patient is improved.

In some embodiments, the ultrasound component 130 is an ultrasound element, such as an ultrasound transducer and/or ultrasound transducer array. For example, the ultrasound component 130 can be configured to generate and emit ultrasound energy into the anatomy 102 in response to transmission of an electrical signal to the ultrasound component 130. Unlike the ultrasound component 120, which is used of ultrasound imaging, the ultrasound component 130 need not be configured to receive ultrasonic echoes reflected the anatomy 102 and generate a representative electrical signal. For example, in some embodiments, the ultrasound component 130 is not an ultrasound element that generates ultrasound energy. Rather, the ultrasound components 130 can be an intermediate component that is configured to deliver ultrasound energy generated by an ultrasound component separate from the ultrasound device 110 (e.g., an external ultrasound transducer positioned outside of the body of the patient). For ultrasound therapy, the center frequency of the ultrasound component 130 can be between 1 kHz and 5 MHz, for example, including values such as 50 kHz, 500 kHz, 1 MHz, 3 MHz, and/or other suitable values both larger and smaller. In some embodiments, the frequency of the ultrasound component 130 is tunable. For example, the frequency of the emitted ultrasonic energy can be modified by the voltage of the applied electrical signal and/or the application of a biasing voltage to the ultrasound component 130.

In some embodiments, such as when the ultrasound components 120 and 130 both include ultrasound transducers, the ultrasound components 120 and 130 can be configured to generate and emit ultrasound energy, and to generate electrical signals representative of the received ultrasound echoes. One of the ultrasound components 120, 130 can be operated in diagnostic and/or imaging mode (generates and emits ultrasound energy, and generates electrical signals representative of the received ultrasound echoes), while the other of the ultrasound components 120, 130 is operated in therapeutic mode (generates and/or emits ultrasound energy).

In some embodiments, the ultrasound device 110 includes a treatment component 145. For example, the treatment component 145 can include a balloon, a stent, a needle, an ablation electrode, mechanical cutting component, a rotational cutting device, an aspiration device, and/or other suitable devices. The treatment component 145 can be a targeted drug delivery device, a drug coated balloon, a drug coated stent, and/or other suitable device configured to deliver a pharmacological agent to the anatomy 102, such as the occlusion 106. For example, the pharmacological agent can be delivered to the anatomy 102 by the treatment component 145 after the ultrasound therapy is applied to the anatomy 102 by the ultrasound component 130. In other embodiments, the ultrasound device 110 omits the treatment component 145.

In some embodiments, it is advantageous to position the components 120, 130, and/or 145 in one compact transducer assembly 200 because doing so can minimize the length of a relatively stiffer segment of the flexible elongate member 116. In some other embodiments, it is advantageous to position the ultrasound component 120, 130, and/or 145 in separate transducer assemblies and couple them together with flexible members or flexible joints. This is so because the each of the transducer assembly carrying only one ultrasound component tends to be shorter in length. When coupled together by flexible members/joints, the transducer assemblies can be steerable through tortuous vasculature like cars of a train.

Generally, the ultrasound components 120, 130, and/or 145 are positioned at the distal portion of the flexible elongate member 116. The relative positioning of the ultrasound components 120, 130, and/or 145 can vary in different embodiments. In the illustrated embodiment, the diagnostic and/or imaging ultrasound component 120 is positioned proximally of the therapeutic ultrasound component 130. In other embodiments, the therapeutic ultrasound component 130 is positioned proximally of the diagnostic and/or imaging ultrasound component 120. In embodiments which include the treatment component 145, the treatment component 145 can be positioned proximally of the ultrasound components 120 and/or 130, distally of the ultrasound components 120 and/or 130, or between the ultrasound components 120 and/or 130.

The ultrasound components 120 and/or 130 can include one or more electrical conductors extending along the length from the flexible elongate member 116. The electrical conductor(s) are in communication with the ultrasound components 120, 130 at the distal portion 114, and an interface 156 at the proximal portion 112. The electrical conductors carry electrical signals between the ultrasound processing system 160 and the ultrasound components 120, 130. For example, activation and/or control signals can be transmitted from the ultrasound processing system 160 to the ultrasound components 120, 130 via the electrical conductors. Electrical signals representative of the reflected ultrasound echoes can be transmitted from the ultrasound components 120 and/or 130 to the ultrasound processing system 160 via the electrical conductors. In some embodiments, the same electrical conductors can be used for communication between the ultrasound processing system 160 and the ultrasound components 120 and/or 130. In other embodiments, different electrical conductors of the ultrasound device 110 can be used for communication between the ultrasound processing system 160 and the ultrasound component 120, and between the ultrasound processing system 160 and the ultrasound component 130.

The ultrasound device 110 includes an interface 156 at the proximal portion 112 of the flexible elongate member 116. In some embodiments, the interface 156 can include a handle. For example, handle can include one or more actuation mechanisms to control movement of the device 110, such as deflection of the distal portion 114. In some embodiments, the interface 156 can include a telescoping mechanism that allows for pullback of the device 110 through the lumen. In some embodiments, the interface 156 can include a rotation mechanism to rotate one or more components of the device 110 (e.g., the flexible elongate member 116, the ultrasound components 120, 130). In some embodiments, the interface 156 includes a user interface component (e.g., one or more buttons, a switch, etc.) for a medical professional to selectively activate the ultrasound component 120 for imaging or the ultrasound component 130 for therapy. In other embodiments, a user interface component of the PIM 150, the ultrasound processing system 160 and/or the monitor 170 allows a medical profession to selectively activate the ultrasound component 120 for imaging or the ultrasound component 130 for therapy. A conduit including, e.g., electrical conductors, extends between the interface 156 and the connector 108. The connector 108 can be configured to mechanically and/or electrically couple the device 110 to the PIM 150.

The ultrasound processing system 160, the PIM 150, and/or the intravascular device 110 (e.g., the interface 156, the ultrasound components 120 and/or 130, etc.) can include one or more controllers. The controllers can be integrated circuits, such as application specific integrated circuits (ASIC), in some embodiments. The controllers can be configured to select the particular transducer element(s) to be used for transmit and/or receive, to provide the transmit trigger signals to activate the transmitter circuitry to generate an electrical pulse to excite the selected transducer element(s), and/or to accept amplified echo signals received from the selected transducer element(s) via amplifiers of controllers. Multiple ASIC configurations with various numbers of master circuits and slave circuits can be used to create a single ultrasound wave or multi-firing ultrasound wave device.

In some embodiments, the PIM 150 performs preliminary processing of the ultrasound echo data prior to relaying the data to the computer or console 106. In examples of such embodiments, the PIM 150 performs amplification, filtering, and/or aggregating of the data. In an embodiment, the PIM 150 also supplies high- and low-voltage DC power to support operation of the ultrasound device 110 including circuitry associated with the ultrasound components 120 and/or 130. The PIM 150 can be an isolation device as, in various surgical settings, patient safety requirements mandate physical and electrical isolation of the patient from one or more high voltage components.

The ultrasound processing system 160 receives imaging data (e.g., electrical signals representative of the ultrasound echo data) from the ultrasound component 120 by way of the PIM 150. The ultrasound processing system 160 can include processing circuit, such as processor and/or memory. The ultrasound processing system 160 processes the data to reconstruct an image of the anatomy. The ultrasound processing system 160 outputs image data such that an image of the anatomy 102, such as a cross-sectional IVUS image of a vessel, is displayed on the monitor 170. The ultrasound processing system 160 and/or the monitor 170 can include one or more user interface elements (e.g., touchscreen, keyboard, mouse, virtual buttons on a graphical user interface, physical buttons, etc.) to allow a medical professional to control the device 110, including one or more parameters of the ultrasound components 120, 130.

Figure 2:
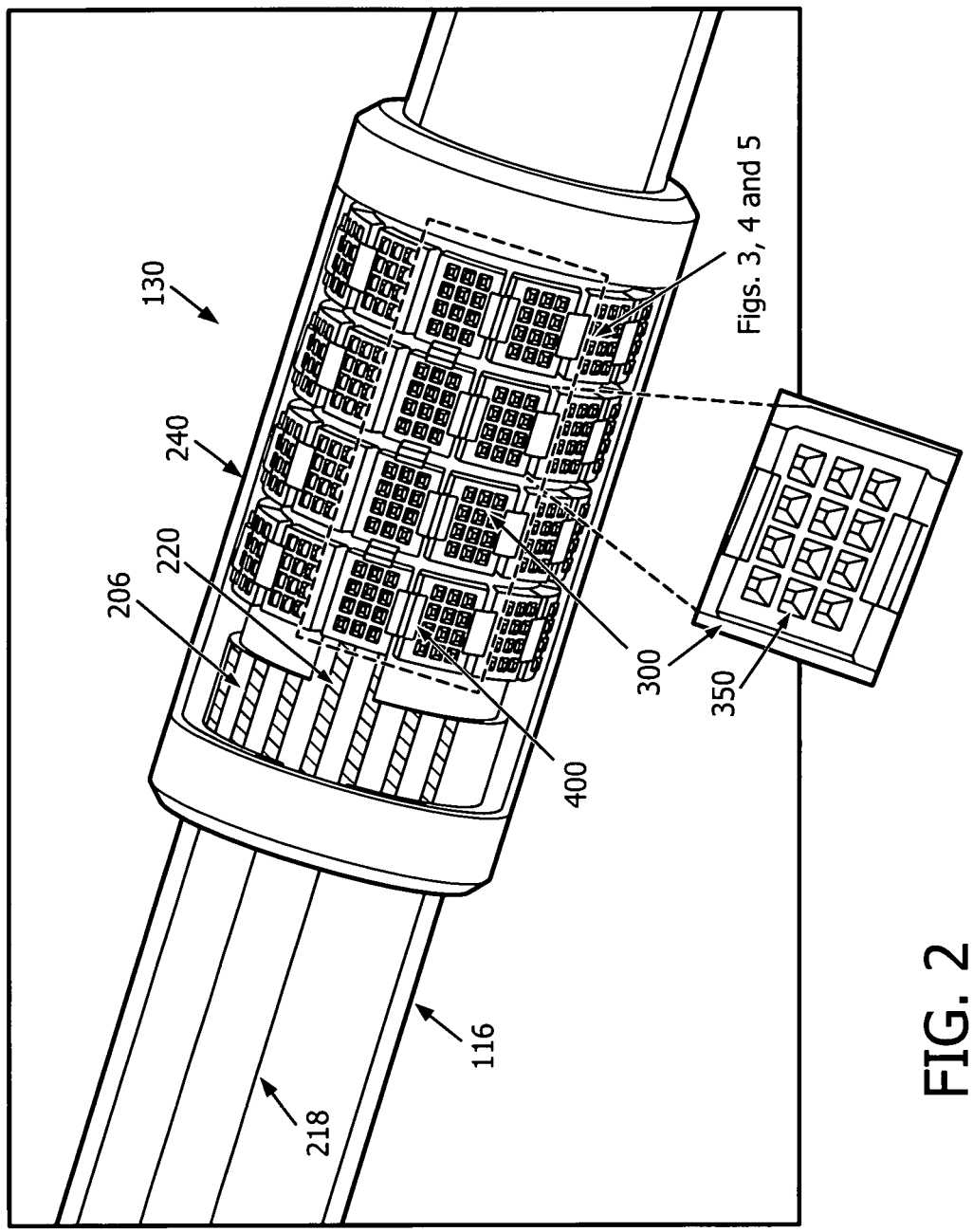
FIG. 2 is a diagrammatic top view of an transducer assembly with an ultrasound transducer array in a configuration, according to aspects of the present disclosure.

Referring now to FIG. 2, shown there in a diagrammatic top view of the transducer assembly 200, according to aspects of the present disclosure. The transducer assembly 200 includes the ultrasound component 130. In some embodiments represented by FIG. 2, the ultrasound component is a transducer array and is therefore sometimes referred to as the transducer array 130. The transducer array 130 includes a plurality of subarrays 300. In some implementations, the subarrays 300 are rectangular in shape and positioned side-by-side next to one another to form the transducer array 130. As shown in the enlarged view of one of the subarrays 300, each of the subarrays 300 includes a plurality of transducers 350. In some embodiments, a subarray 300 can include 4 to 32 transducers 350. Further, in some implementations, the transducers 350 are mounted on a substrate. In some instances, the substrate is planar. In some other instances, the substrate is a semiconductor substrate, such as a silicon substrate. In still other instances, the substrate is a glass substrate.

In some embodiments, a support structure 240 is formed over the transducer array 130 increase robustness of the transducer assembly 200 while maintaining the pliability thereof. In some implementations, the support structure 240 can be selected from biocompatible plastics, such as low-durameter PEBAX or nylon and/or super elastic alloys. The support structure 240 can be formed over the transducer array through molding, adhesive filling, welding, and heat shrinking. In some embodiments, to eliminate air pockets when the transducer array 130 operates at a first frequency range to obtain ultrasound imaging data, the transducer array 130 is filled with a flexible matching layer. For example, the flexible matching layer can be a low-durameter plastic over-molded over the transducer array 130 or a saline solution can be used to fill the space between the transducer array 130 and the support structure 240.

As shown in FIG. 2, the subarrays 300 are interconnected by flexible circuits 400. The flexible circuits 400 connect subarrays 300 along a direction parallel to the longitudinal axis LA of the flexible elongate member 116 and a direction around a circumference of the longitudinal axis LA. The transducer assembly 200 includes a connection interface 220. The connection interface 220 includes conductive traces, distal ends of which are connected to each of the subarrays 300. The proximal end of the connection interface 220 is connected to a control circuit 206. In some implementations, the control circuit 206 includes a plurality of control logic dies mounted on a flexible circuit. The control circuit 206 transmits and receives electrical signals to and from the ultrasound processing system 160 shown in FIG. 1 via electrical conductors of the conductive element 218. The control circuit 206 activates and controls the transducer array 130. In some embodiments, the control circuit 206 controls the transducer array 130 on a subarray level. That is, the control circuit 206 can selectively activate one or more subarrays 300 at a time. For example, in cases where the transducer array 130 is separated into two or more segments, the control circuit 206 can activate and control these segments separately.

The transducers 350 can be capacitive micromachined ultrasound transducers (CMUTs) or piezoelectric micromachined ultrasound transudcers (PMUTs). In the embodiments where the transducer 350 is a CMUT, the transducer 350 includes a diaphragm that is formed over a vacuum gap in a dielectric layer on a substrate, usually made of silicon. The CMUT further includes an electrode over the diaphragm and another electrode across the air gap from the diaphragm. The diaphragm of the CMUT can be excited by an alternating current (AC) electrical signal across the electrodes to emit an ultrasound pulse. The frequency or frequency range of the ultrasound pulse emitted by the CMUT depends on the amplitude of the electrical signal. The CMUT operates at a higher frequency or a higher frequency range when the amplitude of the electrical signal is greater. Reversely, an ultrasound pulse can cause deflection of the diaphragm into or away from the air gap, resulting in a change in capacitance across the electrodes. By measuring the change in capacitance, properties of the ultrasound pulse can be determined. In some embodiments, a direct current (DC) bias voltage can be applied across the electrodes of the CMUT to pre-tension the diaphragm. Based on the level of the bias voltage, the diaphragm can be subject to different level of pre-tension. In general, the higher the tension present in the diaphragm, the higher the frequency at which the CMUT emits. In some embodiments, the subarray 300 includes a plurality of CMUT transducer 350. The bias voltage can be applied to the whole or part of the transducer array 130 by the control circuit 206 (shown in FIG. 2) or by the ultrasound processing system 160 via electrical conductors of the conductive element 218. The effective size of the subarray 300 can be enlarged by connecting the diaphragms of the transducers 350 therein and operating them in parallel. That is, the frequency or frequency range at which the subarray 300 becomes lower when more CMUT transducers 350 in the subarray 300 operate in parallel to increase the effective size of the subarray 300. In some instances, the CMUT transducer 350 includes features described in U.S. patent application Ser. No. 14/812,792, titled "INTRAVASCULAR ULTRASOUND IMAGING APPARATUS, INTERFACE ARCHITECTURE, AND METHOD OF MANUFACTURING," filed Jul. 29, 2015, which is hereby incorporated by reference in its entirety.

In embodiments where the transducer 350 is PMUT, the transducer 350 includes a well located in a substrate and a piezoelectric transducer membrane disposed over the well. The piezoelectric transducer member includes a top electrode and a bottom electrode. The well is at least partially filled with a backing material. The piezoelectric transducer member can be deflected by an electrical signal applied across the top and bottom electrodes to emit an ultrasound pulse. Reversely, an ultrasound pulse can cause deformation of the piezoelectric transducer membrane, resulting in a change of voltage across the top and bottom electrodes. The frequency or frequency range at which the PMUT emits the ultrasound pulse depends on the thickness and material of the piezoelectric transducer membrane and thickness and material of the backing material. In general, the PMUT operates at a higher frequency or a higher frequency range if the thickness of the piezoelectric transducer membrane and the backing material is reduced. In some instances, the PMUT operates at a higher frequency or a higher frequency range if the piezoelectric transducer membrane is made of a more rigid material.

Figure 3:
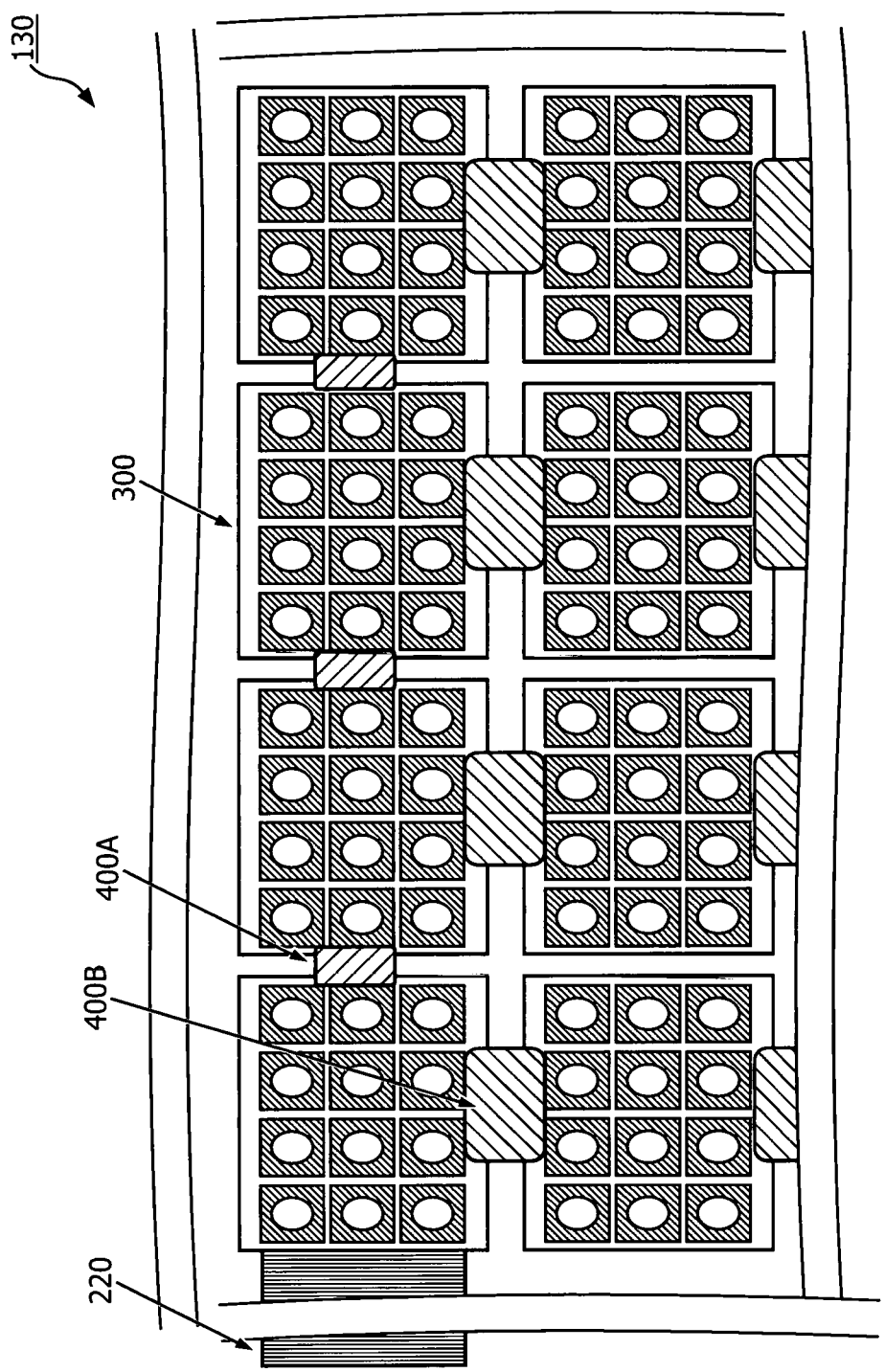
FIG. 3 is a diagrammatic enlarged view of subarrays of an transducer assembly, according to aspects of the present disclosure.

Referring now to FIG. 3, shown therein is a diagrammatic enlarged view of the segment of subarrays 300 of the transducer array 130, according to aspects of the present disclosure. For illustration purposes, each of the subarrays 300 in FIG. 2-5 includes 12 transducers 350. However, embodiments of subarrays 300 with more transducers 350 are envisioned. In some embodiments, a subarray 300 can include 4 to 32 transducers 350. The subarrays 300 are interconnected along the longitudinal axis LA of by flexible circuits 400A and are interconnected circumferentially around the longitudinal axis LA by flexible circuits 400B. The subarrays 300 are electrically connected to the control circuit 206 via the connection interface 220. In some embodiments, all transducers 350 in the subarrays 300 of the transducer array 130 are all PMUTs. In some embodiments, all transducers 350 in the subarrays 300 of the transducer array 130 are CMUTs.

In the embodiments where all transducers 350 are either PMUTs or CMUTs, the control circuit 206 can transmit a first electrical signal to the transducer array 130 such that the transducer array 130 operates at a first frequency range to obtain ultrasound imaging data of a target site (such as occlusion 106 within a body lumen 104; and the control circuit 206 can transmit a second electrical signal to the transducer array 130 such as the transducer array 130 operates at a second frequency range to apply an ultrasound therapy within the body lumen 104. In these embodiments, the first electrical signal has a higher amplitude or higher voltage than the second electrical signal. The first frequency falls between 10 MHz and 70 MHz and the second frequency fall between 1 KHz to 20 MHz, and in some cases, between 1 KHz and 5 MHz. The first frequency range has a first median and the second frequency range has a second median. The first median is higher than the second median. In these embodiments, in response to the first electrical signal, the transducer array 130 operates at the first frequency to function as an ultrasound imaging device. In addition, in response to the second electrical signal, the transducer array 130 operates at the second frequency to function an ultrasound therapy applicator.

In the embodiments where all transducers 350 are CMUTs, the control circuit 206 or a voltage source external to the control circuit 206 can also subject the CMUT transducers 350 to a bias voltage such that the diaphragms of the transducers 350 are pre-deflected or pre-tensioned to emit ultrasound pulses at a higher frequency. In some implementations, when the control circuit 206 transmits the first electrical signal to the transducer array 130, the control circuit 206 can simultaneously subject the transducer array 130 to the bias voltage.

Figure 4:
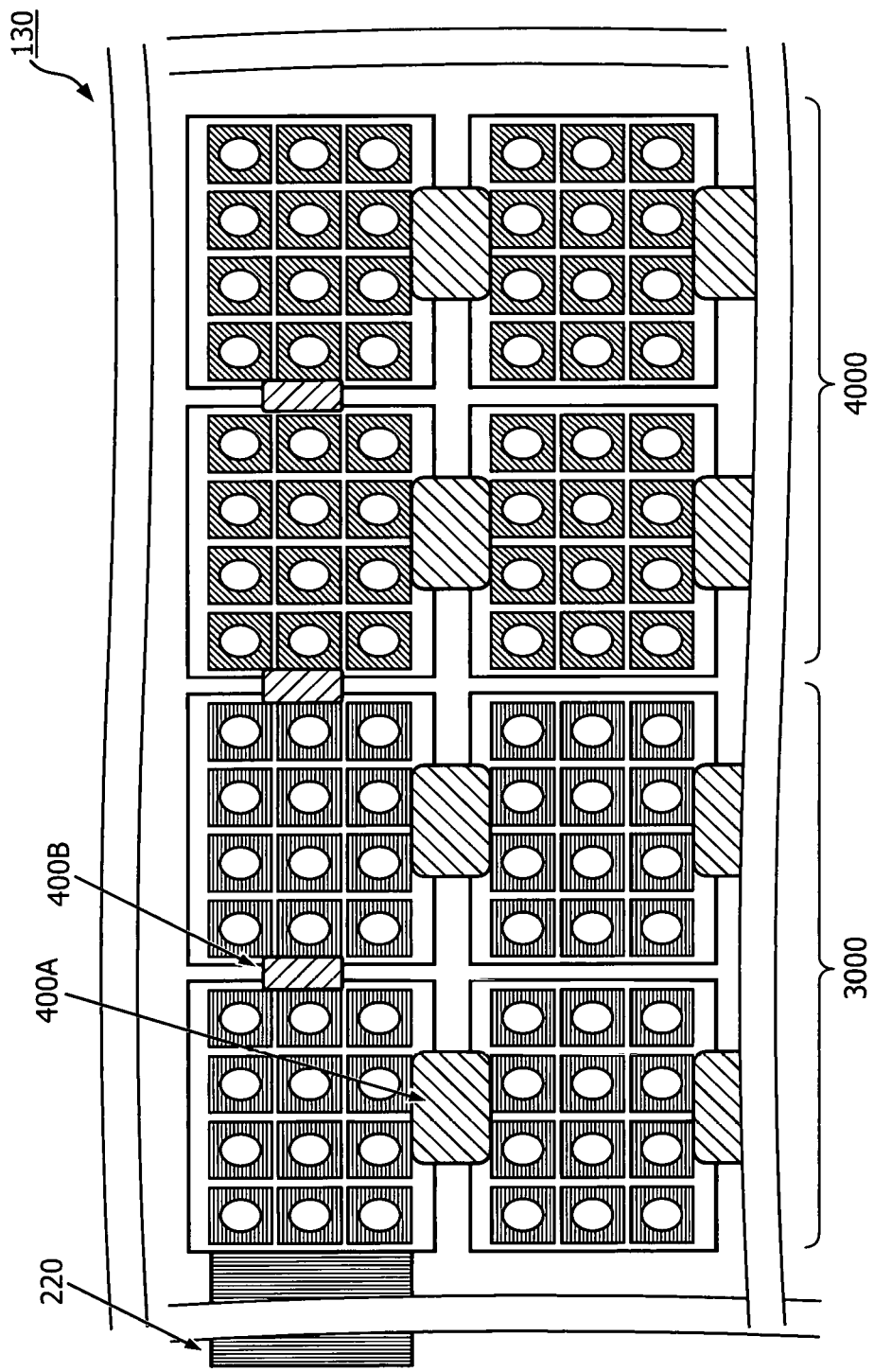
FIG. 4 is a diagrammatic enlarged view of subarrays of an transducer assembly, according to aspects of the present disclosure.

Referring now to FIG. 4, shown therein is a diagrammatic enlarged view of a segment of subarrays 300 of the transducer array 130, according to aspects of the present disclosure. As shown in FIG. 4, in some embodiments, the transducer array 130 includes a proximal half 3000 and a distal half 4000, with each half being cylindrical in shape and positioned circumferentially around the longitudinal axis LA. In some embodiment, the control circuit 206 can activate and control the proximal half 3000 and the distal half 4000 separately. In some implementations, the transducer array 130 includes CMUT transducers 350 throughout or the PMUT transducer 350 throughout. The control circuit 206 can transmit the first electrical signal to the proximal half 3000 and the second electrical signal to the distal half 4000. In some other implementations, the proximal half 3000 includes PMUT transducers 350 and the distal half 4000 includes CMUT transducers 350. In still other implementations, the proximal half 3000 includes CMUT transducers 350 and the distal half 4000 includes PMUT transducers 350. In another embodiment, all transducers 350 in the transducer array 130 are CMUTs. The proximal half 3000 is subject to a first bias voltage and the distal half 4000 is subject to a second bias voltage. The first bias is different from the second bias. In some instances, the first bias is zero volts (no bias) and the second bias is a non-zero bias, which pre-tensions the diaphragms of the CMUT transducers so that the transducers operate at a higher frequency or a higher frequency range.

Figure 5:
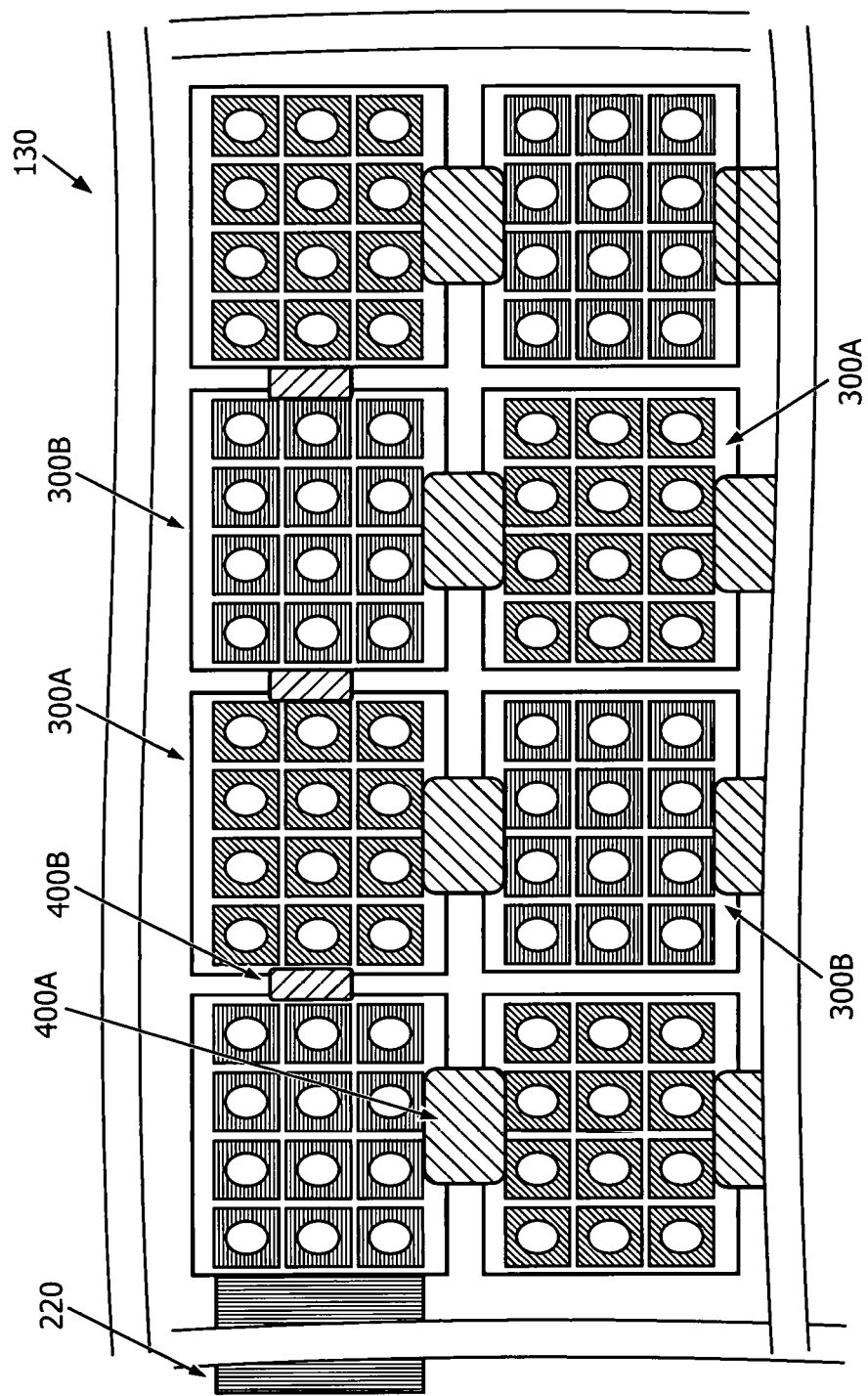
FIG. 5 is a diagrammatic enlarged view of subarrays of an transducer assembly, according to aspects of the present disclosure.

Reference is made to FIG. 5. Shown therein is a diagrammatic enlarged view of the segment of subarrays 300 of the transducer array 130, according to aspects of the present disclosure. In the embodiments shown in FIG. 5, first subarrays 300A and second subarrays 300B are positioned alternately next to one another. In these embodiments, first subarrays 300A are distributed evenly across the transducer array 130 and so are the second subarrays 300B. In some embodiments, the first subarrays 300A and the second subarrays 300B include CMUT transducers 350 throughout and the control circuit 206 is configured to transmit a first electrical signal to the first subarrays 300A and a second electrical signal to the second subarrays 300B. In response to the first electrical signal, the CMUT transducers 350 operate at the first frequency range to obtain ultrasound imaging data. In response to the second electrical signal, the CMUT transducers 350 are operable at the second frequency range to apply an ultrasound therapy. In some instances, the transducer 130 includes CMUT transducers 350 throughout and the control circuit 206 can selectively subject the first subarrays 300A to a first bias and the second subarrays to a second bias. The first bias is different from the second bias. In some implementations, the first bias is zero. In still other embodiments, the first subarrays 300A include PMUT transducers 350 throughout and the second subarrays 300B include CMUT transducers 350 throughout.

Referring back to FIG. 1, the ultrasound device 110 includes a treating component 145 in some embodiments. For example, the treatment component 145 can include a balloon, a stent, a needle, an ablation electrode, mechanical cutting component, a rotational cutting device, an aspiration device, and/or other suitable devices. The treatment component 145 can be a targeted drug delivery device, a drug coated balloon, a drug coated stent, and/or other suitable device configured to deliver a pharmacological agent to a target site in the anatomy 102, such as the occlusion 106.

Figure 6A:
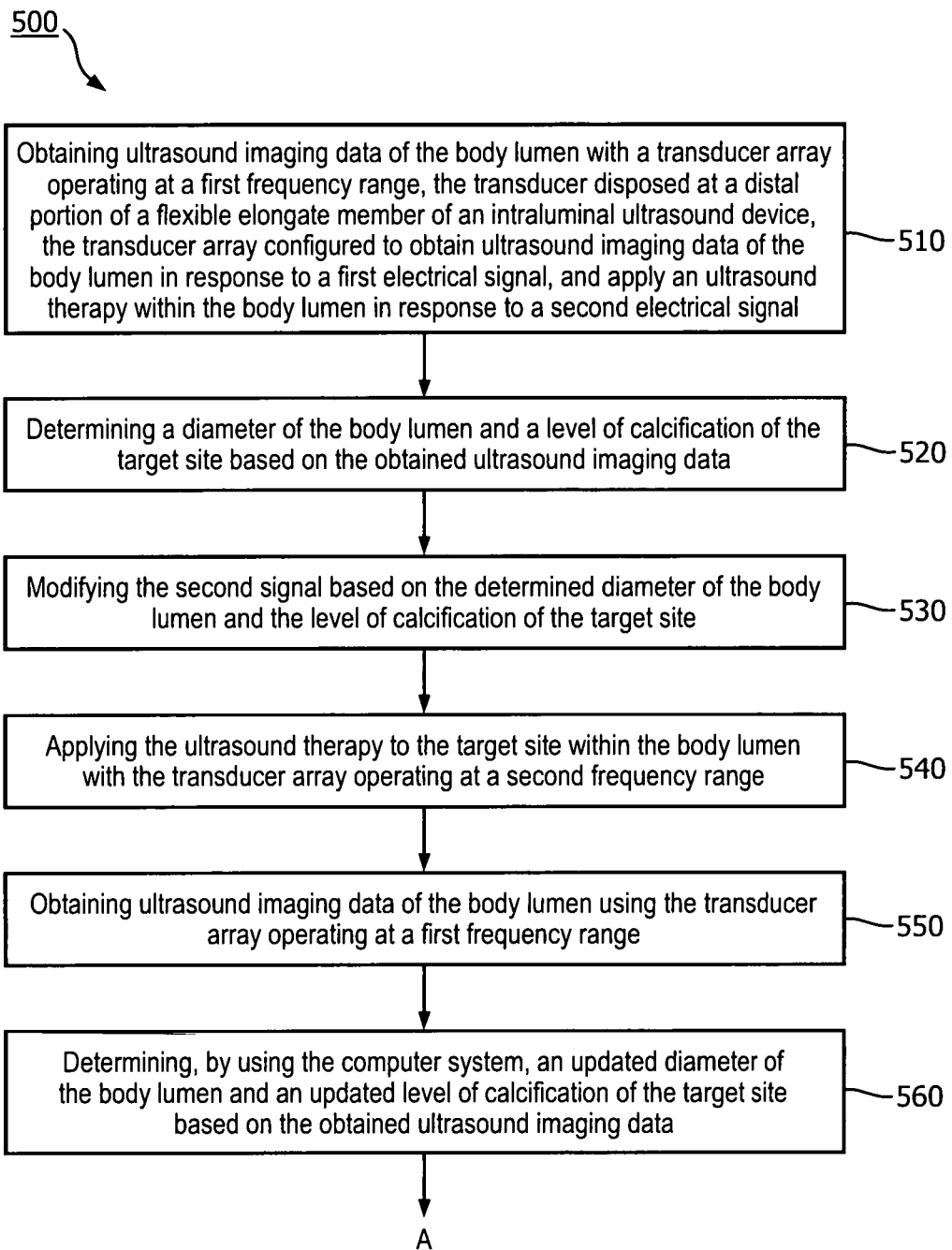
FIGS. 6A and 6B are flow diagrams of a method of treating a target site using an ultrasound device according to aspects of the present disclosure.
Figure 6B:
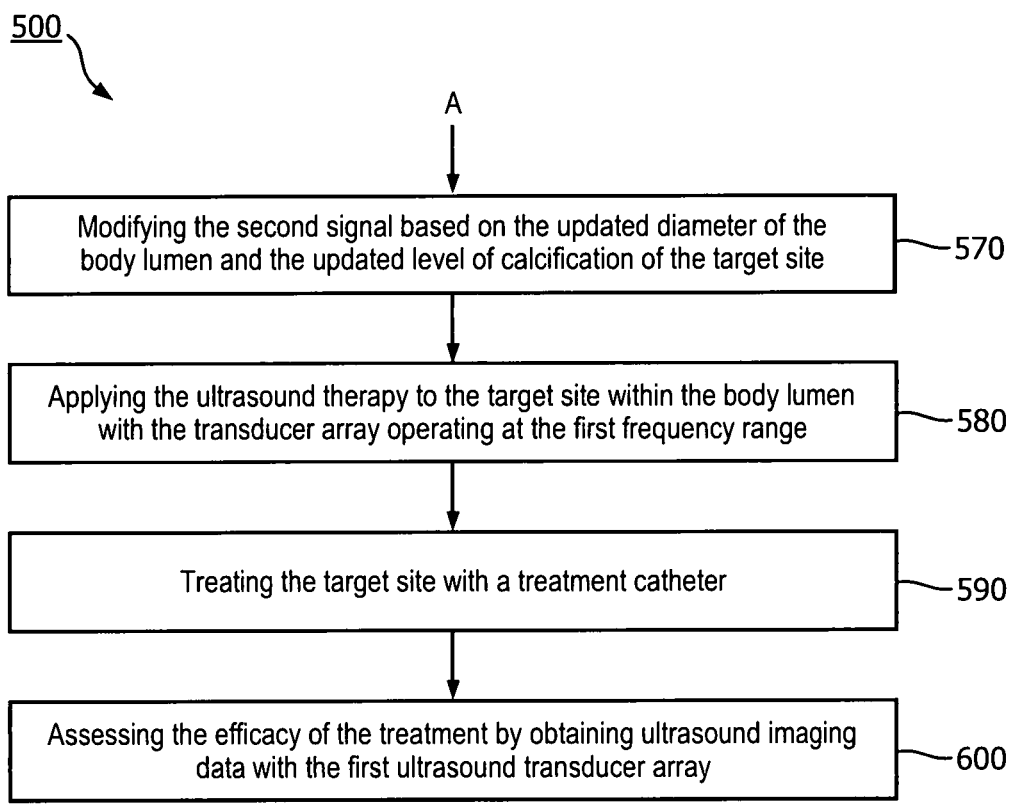

FIGS. 6A and 6B show a flow diagram of a method 500 of treating a target site, such as the occlusion 106 in FIG. 1 within a body lumen of a patient, according to aspects of the present disclosure. The method 500 includes operations 510, 520, 530, 540, 550, 560, 570, 580, 590, and 600. For illustration purposes, the operations of method 500 will be described with reference to FIGS. 1 and 2. At operation 510, ultrasound imaging data of the body lumen 104 is obtained with use of the transducer array 130 operating at a first frequency range. The transducer array 130 is disposed at the distal portion 114 of the flexible elongate member 116 of the intraluminal ultrasound device 110. The flexible elongate member 116 is configured to be positioned within the body lumen 104 of a patient. The transducer array 130 is circumferentially positioned around the longitudinal axis LA of the flexible elongate member 116 and is configured to obtain ultrasound imaging data of the body lumen 104 in response to a first electrical signal. The transducer array 130 can also apply an ultrasound therapy in response to a second electrical signal.

At operation 520, a diameter of the body lumen 104 and a level of calcification of the target site, such as the occlusion 106 in FIG. 1, are determined based on the ultrasound imaging data obtained at operation 510. In general, a target site, such as occlusion 106 in FIG. 1, tends to reflect more ultrasound energy when it has a higher level of calcification. That is, by measuring the intensity of the ultrasound signal associated with ultrasound echoes reflected from the target site, the level of calcification of the target site can be determined. For example, virtual histology (VH) methods and algorithms can be used to determine the boundary of the blood vessel wall defining the body lumen 104 and the density of a target site, such as the occlusion 106. Detecting and characterizing plaque using IVUS with VH are described in, for example, U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NONINVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entireties.

At operation 530, a second electrical signal, usually a default or an initial electrical signal, is modified based on the diameter of the body lumen 104 and the level of calcification of the target site determined at operation 520. Depending on the diameter of the body lumen 104 where the target site is positioned and the level of calcification of the target site, effective treatment of the target site requires an ultrasound therapy involving ultrasound pulses with different frequencies, different pulse amplitudes, and different pulse lengths. Once the diameter of the body lumen 104 and the level of calcification of the target site are determined at operation 520, an ultrasound processing system 160 in communication of the ultrasound device 110 can modify the second electrical signal to be transmitted to the transducer array 130 for effective treatment of the target site.

At operation 540, an ultrasound therapy is applied to the target site within the body lumen 104 with the transducer array 130, operating in response to the modified second electrical signal.

At operation 550, ultrasound imaging data of the body lumen 104 is obtained using the transducer array 130, which operates at the first frequency range in response to the first electrical signal. To assess the efficacy of the ultrasound therapy applied at operation 540, ultrasound imaging data of the lumen 104 is obtained again by the transducer array 130, in response to the first electrical signal.

At operation 560, an updated diameter of the body lumen 104 and an updated level of calcification of the target site is determined by the ultrasound processing system 160, based on the ultrasound imaging data obtained at operation 550. As an ultrasound therapy has been applied to the target site, the diameter of the body lumen 104 and the level of calcification of the target site may have reduced. To determine the updated diameter of the body lumen 104 and the updated level of calcification of the target, ultrasound imaging data of the lumen 104 is obtained again with use of the transducer array 130.

At operation 570, the second electrical signal is again modified by the ultrasound processing system 160 based on the updated diameter of the body lumen 104 and the updated level of calcification of the target site. Based on parameters stored in the ultrasound processing system 160, the ultrasound processing system 160 can determine whether further ultrasound therapies are required. If no further ultrasound therapies are required, method 500 would skip operation 580 and proceed directly to operation 590. If further ultrasound therapies are required, the ultrasound processing system 160 modifies the second electrical signal for effective treatment of the target site.

At operation 580, the ultrasound therapy is applied to the target site within the body lumen 104 while the transducer array 130 operates at a second frequency range in response to the modified second electrical signal.

At operation 590, the target site is treated with the treatment component 145 disposed on the distal portion 114 of the ultrasound device 110. In some instances, the treatment component 145 is incorporated in the transducer assembly 200. In some other instances, the treatment component 145 is separate from the transducer assembly 200 and is distal to the transducer assembly 200.

At operation 600, to assess the efficacy of the treatment by the treatment component 145, ultrasound imaging data of the body lumen 104 is obtained using the first ultrasound transducer array 124B.

The systems, devices, and methods of the present disclosure can include features described in U.S. Provisional App. No. 62/545,944, filed on an even date herewith, U.S. Provisional App. No. 62/545,951, filed on an even date herewith, U.S. Provisional App. No. 62/545,927, filed on an even date herewith, and/or U.S. Provisional App. No. 62/545,888, filed on an even date herewith, the entireties of which are hereby incorporated by reference herein.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal ultrasound device, comprising:
   a flexible elongate member configured to be positioned within a body lumen of a patient, the flexible elongate member including a distal portion and a longitudinal axis;
   a transducer array disposed at the distal portion of the flexible elongate member and circumferentially positioned around the longitudinal axis of the flexible elongate member, wherein the transducer array comprises a plurality of micromachined ultrasound transducers (MUTs) arranged into a plurality of sub-arrays that are inter-connected by a plurality of flexible circuits, wherein a first sub-array of the transducer array is configured to obtain ultrasound imaging data of the body lumen including an occlusion of the body lumen in response to a first electrical signal applied to each of the MUTs in the first sub-array via the plurality of flexible circuits, and a second sub-array of the transducer array is configured to apply an ultrasound therapy within the body lumen in response to a second electrical signal applied to each of the MUTs in the second sub-array via the plurality of flexible circuits; and
   a processing system configured to treat the occlusion by applying ultrasound therapy to the occlusion using the second sub-array of the transducer array and by administering a variable dose of a pharmacological agent to the occlusion during the application of the ultrasound therapy, the processing system further configured to image the occlusion during the treatment of the occlusion using the first sub-array of the transducer array and to vary the dose of the pharmacological agent during the treatment of the occlusion based on size and echogenicity of the occlusion determined from the imaging of the occlusion.

2. The intraluminal ultrasound device of claim 1, wherein the MUTs of the first sub-array are configured to operate at a first frequency range in response to the first electrical signal and wherein the MUTs of the second sub-array are configured to operate at a second frequency range different from the first frequency range in response to the second electrical signal.

3. The intraluminal ultrasound device of claim 2, wherein the first frequency range and the second frequency range do not overlap.

4. The intraluminal ultrasound device of claim 2, wherein the first frequency range comprises frequencies between 10 MHz and 70 MHz and the second frequency range comprises frequencies between 1 KHz and 20 MHz.

5. The intraluminal ultrasound device of claim 1, further comprising a control circuit in communication with the transducer array, the control circuit being configured to generate the first electrical signal and the second electrical signal.

6. The intraluminal ultrasound device of claim 5, wherein a voltage of the first electrical signal is different than a voltage of the second electrical signal.

7. The intraluminal ultrasound device of claim 5, wherein the plurality of MUTs comprises a plurality of piezoelectric micromachined ultrasound transducers (PMUTs).

8. The intraluminal ultrasound device of claim 5, wherein the plurality of MUTs comprises a plurality of capacitive micromachined ultrasound transducers (CMUTs).

9. The intraluminal ultrasound device of claim 8, wherein each of the plurality of CMUTs is configured to receive a bias voltage from the control circuit and the control circuit is configured to control the bias voltage applied to the plurality of CMUTs to adjust a pre-tension of diaphragms of the CMUTs wherein higher pre-tension causes the CMUT to emit at higher frequency.

10. The intraluminal ultrasound device of claim 1, wherein: the first sub-array configured to obtain ultrasound imaging data and the second sub-array configured to apply the ultrasound therapy within the body lumen comprise separate assemblies coupled together with flexible members or flexible joints.

11. The intraluminal ultrasound device of claim 1, wherein:
    the plurality of MUTs comprises a first plurality of piezoelectric micromachined ultrasound transducers (PMUTs) and a second plurality of PMUTs,
    each of the first plurality of PMUTs includes a transducer membrane of a first thickness, and
    each of the second plurality of PMUTs includes a transducer membrane of a second thickness different from the first thickness.

12. The intraluminal ultrasound device of claim 1, wherein:
    each of the MUTs in the first sub-array is configured to receive a first direct current (DC) bias voltage via the plurality of flexible circuits to provide a pre-tension of diaphragms of the MUTs of the first sub-array causing the MUTs of the first sub-array to emit at a first frequency, and
    each of the MUTs in the second sub-array is configured to receive a second DC bias voltage that is different from the first bias voltage via the plurality of flexible circuits to provide a pre-tension of diaphragms of the MUTs of the second sub-array causing the MUTs of the first sub-array to emit at a second frequency different from the first frequency.

13. The intraluminal ultrasound device of claim 12, wherein one of the first and second bias voltages is zero volts.

14. The intraluminal ultrasound device of claim 1, wherein the plurality of MUTs comprises a plurality of capacitive micromachined ultrasound transducers (CMUTs) and a plurality of piezoelectric micromachined ultrasound transducers (PMUTs).

15. A system for treating a target site within a body lumen of a patient comprising:
    an intraluminal ultrasound device comprising:

a flexible elongate member configured to be positioned within a body lumen of a patient, the flexible elongate member including a distal portion and a longitudinal axis; and a transducer array disposed at the distal portion of the flexible elongate member and circumferentially positioned around the longitudinal axis of the flexible elongate member, wherein the transducer array comprises a plurality of micromachined ultrasound transducers (MUTs) arranged into a plurality of sub-arrays that are inter-connected by a plurality of flexible circuits, wherein a first sub-array of the transducer array is configured to obtain ultrasound imaging data of the body lumen in response to a first electrical signal applied to the MUTs in the first sub-array via the plurality of flexible circuits, and wherein a second sub-array of the transducer array is configured to apply an ultrasound therapy within the body lumen in response to a second electrical signal applied to the MUTs in the second sub-array via the plurality of flexible circuits, wherein the first sub-array and the second sub-array are at different positions along the longitudinal axis and comprise separate assemblies coupled together with flexible members or flexible joints; and a processing system configured to perform a method of treating the target site, the method including:
controlling the acquisition of ultrasound imaging data using the first sub-array of the transducer array;
determining a diameter of the body lumen and a level of calcification of the target site from the ultrasound imaging data;
modifying the second electrical signal based on the determined diameter of the body lumen and the determined level of calcification of the target site;
applying ultrasound therapy to the target site with the second sub-array of the transducer array operating in response to the modified second electrical signal; and repeating the controlling and determining to determine an updated diameter of the body lumen and an updated level of calcification of the target site.

16. The system of claim 15, wherein the processing system is configured to apply the first and second electrical signals to alternate ultrasound imaging with application of ultrasound therapy.

17. The system of claim 15, wherein the processing system is configured to apply the first and second electrical signals for simultaneous ultrasound imaging and application of ultrasound therapy.

18. The system of claim 17, wherein the processing system is configured to administer a pharmacological agent to the target site through a lumen of the intraluminal ultrasound device.

19. The system of claim 17, wherein the processing system is configured to administer a pharmacological agent to the target site through a lumen of the intraluminal ultrasound device simultaneously with the application of ultrasound therapy.

20. The system of claim 19, wherein the processing system is further configured to administer a variable dose of the pharmacological agent during the application of ultrasound therapy and to vary the dose of the pharmacological agent based on the ultrasound imaging data of the target site detecting a change in echogenicity of the target site indicative of microfractures in the target site.

21. The system of claim 15, wherein the method further includes:
further modifying the second electrical signal based on the determined updated diameter of the body lumen and the determined updated level of calcification of the target site; and
applying further ultrasound therapy to the target site with the second sub-array of the transducer array operating in response to the further modified second electrical signal.

* * * * *